United States Patent
Kang et al.

(10) Patent No.: US 11,497,574 B2
(45) Date of Patent: Nov. 15, 2022

(54) SMART MOBILE CART FOR NURSING AND CARING

(71) Applicant: Smart Ageing Tech Co., Ltd., New Taipei (TW)

(72) Inventors: Shih-Chung Kang, New Taipei (TW); Yi-Chun Tseng, New Taipei (TW); Ting Ju Liu, New Taipei (TW); Ya Han Chou, New Taipei (TW)

(73) Assignee: SMART AGEING TECH CO., LTD., New Taipei (TW)

( * ) Notice: Subject to any disclaimer, the term of this patent is extended or adjusted under 35 U.S.C. 154(b) by 404 days.

(21) Appl. No.: 16/747,703

(22) Filed: Jan. 21, 2020

(65) Prior Publication Data
US 2020/0237471 A1    Jul. 30, 2020

(30) Foreign Application Priority Data

Jan. 28, 2019 (TW) ................................. 108103109

(51) Int. Cl.
| | |
|---|---|
| *A61B 50/13* | (2016.01) |
| *A61B 5/0205* | (2006.01) |
| *A61B 5/00* | (2006.01) |
| *A61B 5/1455* | (2006.01) |
| *A61B 50/15* | (2016.01) |
| *A61B 5/022* | (2006.01) |
| *A61B 5/0245* | (2006.01) |

(52) U.S. Cl.
CPC .............. *A61B 50/13* (2016.02); *A61B 5/002* (2013.01); *A61B 5/02055* (2013.01); *A61B 5/14551* (2013.01); *A61B 50/15* (2016.02); *A61B 5/022* (2013.01); *A61B 5/0245* (2013.01)

(58) Field of Classification Search
CPC ...... A61B 50/13; A61B 5/002; A61B 5/02055; A61B 5/14551; A61B 50/15; A61B 5/022; A61B 5/0245; A61B 50/20; A61G 12/001

See application file for complete search history.

(56) References Cited

U.S. PATENT DOCUMENTS

| | | | | |
|---|---|---|---|---|
| 9,504,447 B2* | 11/2016 | Messina | ................. | H01H 9/161 |
| 9,587,878 B2* | 3/2017 | Paydar | .................... | G01K 3/04 |
| 10,617,299 B2* | 4/2020 | Sanchez | ................. | H04N 7/142 |
| 2005/0264649 A1* | 12/2005 | Chang | .................... | F16M 13/00 |
| | | | | 348/E7.079 |
| 2005/0288571 A1* | 12/2005 | Perkins | ................. | A61B 5/742 |
| | | | | 600/407 |
| 2016/0209733 A1* | 7/2016 | Akai | .................... | F16M 13/022 |

\* cited by examiner

*Primary Examiner* — Seung H Lee
(74) *Attorney, Agent, or Firm* — Rosenberg, Klein & Lee

(57) ABSTRACT

The present invention relates to a smart mobile cart for nursing and caring that includes a pole assembly, a flexible gooseneck tube arm and a vital sign sensing device. The flexible gooseneck tube arm has two ends, one of which the two ends is connected with the pole assembly and another end is configured with a device connector. A mobile device is attached to the smart mobile cart through the device connector. The vital sign sensing device is placed on the smart mobile cart through a device convenient carrier. The pole assembly, the flexible gooseneck tube arm, and the device convenient connector are configured to have a ground height adjustable above from a ground level, so as to provide the mobile device and the vital sign sensing device at different ground clearances respectively for a user to operate.

8 Claims, 13 Drawing Sheets

SMART MOBILE CART FOR NURSING AND CARING

CROSS-REFERENCE TO RELATED APPLICATION

The present application claims the priority benefit of Taiwan Invention Patent Application Serial No. 108103109, filed Jan. 28, 2019 in Taiwan intellectual property office, for "Smart Mobile Cart for Nursing", which is incorporated into this application by reference as if fully set forth herein.

COPYRIGHT NOTICE

A portion of this patent document contains material that is subject to copyright protection. The copyright owner has no objection to the facsimile reproduction by anyone of the patent document, as it appears in the Patent and Trademark Office patent files or records, but otherwise reserves all copyright rights whatsoever.

FIELD

The present invention relates to a mobile cart, in particular to a smart mobile cart preferably used in the field of nursing and caring.

BACKGROUND

In the practice field of conventional medical treatment and health care, measurement data of vital signs or physiological signs such as heartbeat, blood pressure and blood sugar were manually written down by nurses or caregivers in a paper sheet in the early days. The first transcription is done at the moment of on-site measurement, and then copied to the official record sheet after returning to the nursing station. Therefore, for nurses in their precious working time, there is actually a lot of time spending in performing these trivial records by hand. And in practice, due to the lack of normal medical manpower, in order to take care of all care recipients as much as possible while avoiding repeated copying, some nurses will only temporarily transcribe the data on their hands or small notes when they perform first transcription, and then formally copy the data on the record sheet as they return to the nursing station.

This kind of handmade medical transcription to record the medical and nursing data will inevitably lead to various problems and inconveniences. For example, when nurses want to carry out on-site physiological measurement, in addition to carrying, moving, and operating various measuring instruments and apparatuses, they also need to perform paper recording by hand at the same time, which not only makes the content too trivial, but also is prone to incur measurement or recording errors, leading to the on-site physiological measurement unreasonably occupying and consuming the nurses too much time. Therefore, when the nurses are too busy, they may automatically skip and omit someone's on-site physiological measurement, which further causes the problem of data disconnection.

Therefore, medical and nursing institutions have successively built electronic information systems to reduce the burden of nursing staff in information recording through the introduction of information systems. However, even if the system is introduced, the nursing staff must make the first transcription by hand, and then key in the transcribed records into the system after returning to the nursing station. Therefore, the nurses still need to implement the first handmade transcription and the second keying-in. In this way, the system cannot provide substantial improvement for the issues of overall time spending, process trivial, error avoidance, process simplification, etc. Medical staff is still likely to skip on-site physiological measurements, and even medical staff has to spend extra time learning some difficult-to-use systems.

Further, the existing tools can't immediately help the institutions to transfer the physiological measurement data recorded by the current systems, integrate the health care information, and then provide them to their families on a regular basis. Even if it is provided to family members, it is only unilateral professional information provided from the perspective of medical treatment and care, such as text about physiological signs and disease symptoms, data, and professional descriptions, which are often full of professional medical terms. For ordinary family members, it is usually not easy to understand the meaning behind these texts, data, and professional descriptions. In this state of incomplete information, it is difficult for the institution to establish positive communication relationship between the care recipients, the family members and the staff.

In a brief summary, the following shortcomings are common in today's medical and nursing institutions: (1) nursing staff repeatedly performs transcription and recording by hands, which is inefficient; it is estimated that only about 40% of the working time of nurses or caregivers are engaged in direct nursing, 45% of time are dealing with miscellaneous affairs and emergencies, and 15% of them are dealing with handwriting or computer data input; especially when the assessment is coming, staving up late to work overtime often indirectly results in a high turnover rate of nursing staff and lack of nursing manpower; (2) handmade recording is easy to cause problems, resulting in data disconnection and poor record accuracy; (3) it is often too late for the management personnel to know the on-site problems; due to the inefficiency and delay of handmade transcription, the supervisor is unable to grasp the scene immediately, and tracking of long-term assessment indicators is not easy, such that prime time processing is often missed; and (4) lack of care communication; the relationship between the family members and the institution is tense; the communication and interaction between the institution and the family members are little, resulting in weak mutual trust and frequent disputes.

Hence, there is a need to solve the above deficiencies/issues.

SUMMARY

The present invention provides a smart mobile cart used in the field of nursing and caring that is easy to use and to be attached or affixed with a mobile device and multiple vital sign sensing devices, to jointly operate with the attached or affixed mobile device and vital sign sensing devices to establish a local or regional internet of thing (IoT) network, to instantly upload or transmit to a smart nursing information platform installed on the mobile device in real time, once vital signs are detected, measured, received or available on site. It is helpful to provide a holistic on-site data integration that seamlessly integrates all kinds of nursing information available on site in real time Hence, as for a nursing aide, a nursing assistant, a resident care attendant, or a personal care attendant, they would no more require to transcribe or write down every data by hand continually, repeatedly, can truly avoid meaningless and time-wasting handwritten routine tasks to realize an automatic information input and an automation for measuring vital signs, and returns to and focuses on their original nursing services and duties, as what they are supposed to do.

In terms of mechanical structure, the smart mobile cart for nursing and caring provided in accordance with the present invention has technical features, such as but not limited to, the height above from the ground level being adjustable and the multiple degree of freedom being adjustable for devices or accessories attached or affixed thereon. The smart mobile cart is able to provide a mobile device or vital sign sensing devices for a user to use or operate at different ground clearances respectively. Any of devices or accessories are attached or affixed to the present smart mobile cart for nursing and caring, via a convenient, a releasable retaining, a detachable or a movable means.

Further to the above, the smart mobile cart in accordance with the present invention is able to assist and render frontline nursing personnel completing on-site measurement operations in a simple, smart, rapid, and automatic way, as well as the smart mobile cart in accordance with the present invention is helpful to build up a smart mobile nursing station, or to provide for a patient or a caring subject to act as a smart beside assistance. The smart mobile cart in accordance with the present invention can further use in operations regarding a nursing, a caring, a home care, or a long-term care, apply for extensive applications, and has un-limited multiple-purpose or multiple-function usages.

Accordingly, the present invention provides a smart mobile cart for nursing and caring that includes: a pole assembly standing upright from a mobile base and having two ends, one of which the two ends is connected with the mobile base; a flexible arm having two ends, one of which the two ends is connected with the pole assembly and another end is configured with a device connector, to render a mobile device attached to the smart mobile cart through the device connector; and an accessory connector connected with the pole assembly in a movable and detachable means and providing for a device convenient carrier to connect with the smart mobile cart through the accessory connector, whereby a vital sign sensing device is placed on the smart mobile cart through the device convenient carrier, wherein the pole assembly, the flexible arm, and the accessory connector are configured to have a height adjustable above from a ground level, so as to provide the mobile device and the vital sign sensing device at different ground clearances respectively for a user to operate.

Preferably, the smart mobile cart further includes: a first accessory connector, connected to the pole assembly in a movable and detachable means and providing for a desk to secure to the smart mobile cart; a second accessory connector, connected to the pole assembly in a movable and detachable means and providing for a handle to secure to the smart mobile cart; a fourth accessory connector, connected to the pole assembly in a movable and detachable means and providing for a mounting base to attach to the smart mobile cart, wherein the buckle base provides for a fourth accessory to affix to the smart mobile cart in a releasable retaining means; and a fifth accessory connector, connected to the pole assembly in a movable and detachable means and providing for an elastic band to attach to the smart mobile cart, wherein the elastic band provides for a fifth accessory to affix to the smart mobile cart in a fastening means.

The present invention further provides a smart mobile cart for nursing and caring that includes: a pole assembly having two ends, one of which the ends connect with a mobile base and stands upright from the mobile base; a flexible arm having two ends, one of which the ends connect with the pole assembly and another is configured with a device connector, to render a mobile device installed with a smart caring platform affixed to the smart mobile cart through the device connector; and an accessory connector, connected with the pole assembly in a movable and detachable means and providing for a device convenient carrier to connect with the smart mobile cart through the accessory connector, to render a vital sign sensing device placed on the smart mobile cart through the device convenient carrier, wherein a wireless communication link is established by configuring a wireless communication protocol between the vital sign sensing device and the mobile device, to render a vital sign signal currently detected by the vital sign sensing device transmitted to the smart caring platform installed on the mobile device in real time.

The present invention further provides a smart mobile cart for nursing and caring that includes: a pole assembly having two ends, one of which the ends connect with a mobile base and stands upright from the mobile base; a support arm having two ends, one of which the ends connect with the pole assembly and another is configured with a device connector, to render a mobile device affixed to the smart mobile cart through the device connector; and an accessory connector, connected with the pole assembly in a movable and detachable means and providing for a device convenient carrier to connect with the smart mobile cart through the accessory connector, to render a vital sign sensing device being placed on the smart mobile cart through the device convenient carrier, wherein by a joint configuration of the pole assembly, the support arm, and the accessory connector, the device connector and the device convenient carrier is enabled to have a height above ground level adjustable so as to provide for a user to operate at different ground clearances respectively.

DESCRIPTION OF THE DRAWINGS

A more complete appreciation of the invention and many of the attendant advantages thereof are readily obtained as the same become better understood by reference to the following detailed description when considered in connection with the accompanying drawing, wherein.

DETAILED DESCRIPTION

Figure 1:
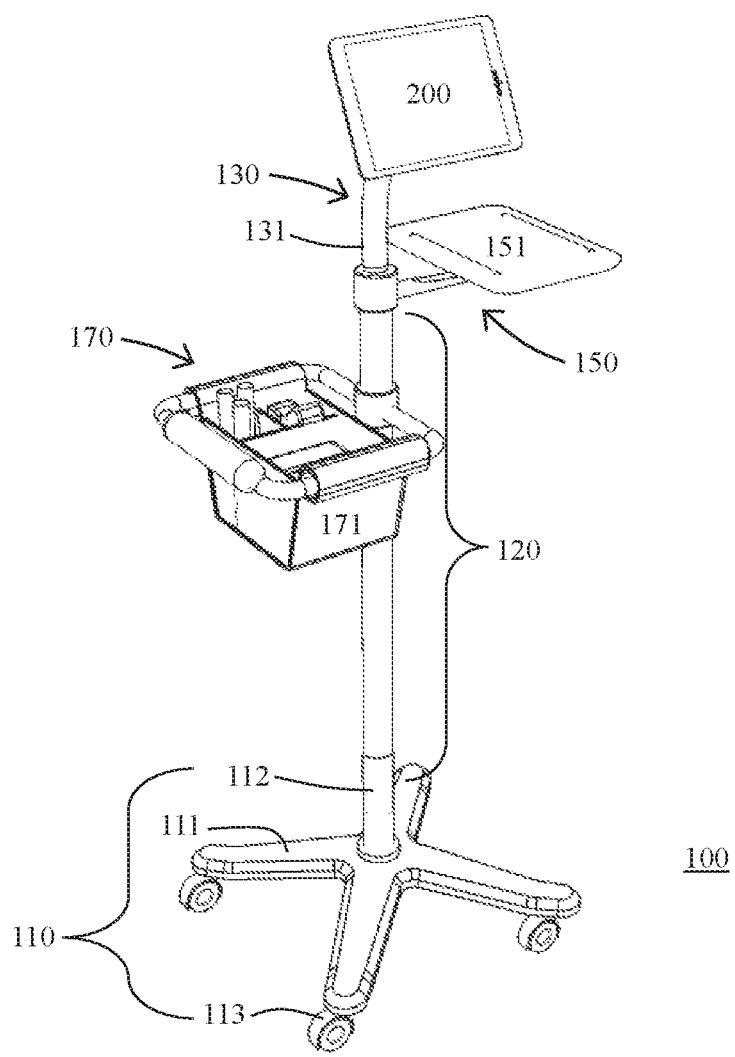
FIG. 1 is a schematic three-dimensional structure diagram illustrating a first embodiment for a nursing and caring smart mobile cart in accordance with the present invention.

The present disclosure will be described with respect to particular embodiments and with reference to certain drawings, but the disclosure is not limited thereto but is only limited by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice.

It is to be noticed that the term "including", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device including means A and B" should not be limited to devices consisting only of components A and B.

The disclosure will now be described by a detailed description of several embodiments. It is clear that other embodiments can be configured according to the knowledge of persons skilled in the art without departing from the true technical teaching of the present disclosure, the claimed disclosure being limited only by the terms of the appended claims.

Figure 2:
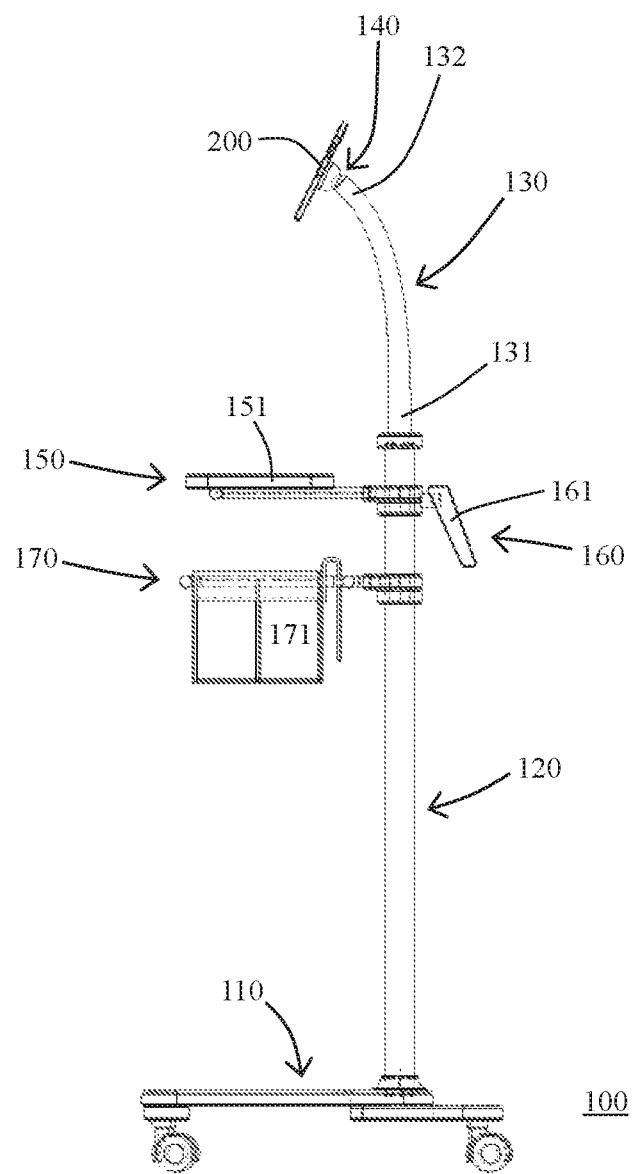
FIG. 2 is a schematic side structure diagram illustrating a second embodiment for the nursing and caring smart mobile cart in accordance with the present invention.

FIG. 1 is a schematic three-dimensional structure diagram illustrating a first embodiment for a nursing and caring smart mobile cart in accordance with the present invention; and FIG. 2 is a schematic side structure diagram illustrating a second embodiment for the nursing and caring smart mobile cart in accordance with the present invention. The smart mobile cart for nursing 100 disclosed in the present invention includes: a mobile base 110, a pole assembly 120, a flexible arm 130, a mobile device connector 140, an optional first accessory connector 150, an optional second accessory connector 160, and an optional third accessory connector 170, wherein the first accessory connector 150, the second accessory connector 160, and the third accessory connector 170 are optional components, namely, the mobile cart 100 can choose all three connectors for configuration, or choose one connector or more connectors for configuration. For example, in the first embodiment disclosed in FIG. 1, the mobile cart 100 only contains the first accessory connector 150 and the third accessory connector 170. In the second embodiment disclosed in FIG. 2, the mobile cart 100 contains the first accessory connector 150, the second accessory connector 160, and the third accessory connector 170.

The mobile base 110 includes a base 111, movable wheels 113 and other components. The base 111 is preferably made of, but not limited to, stainless steel, aluminum alloy, or plastic material. In one embodiment, the base 111 is opened with a plug-in opening at the center, and a section of the plugging sleeve 112 can be provided to connect with the base 111, or a pole assembly 120 is provided to directly plug in and connect with the base 111. In another embodiment, the base 111 and the plugging sleeve 112 are integrally formed or forged. Screws, nuts, or welding can be used for fixing between the plugging sleeve 112 and the base 111 or between the pole assembly 120 and the base 111. The base 111 generally includes a plurality of support feet of unequal length and extending outwards, which can provide the cart 100 with good horizontal stability and make the cart 100 difficult to shake. A group of movable wheels 113 are arranged at the outer end of each support foot. The movable wheel 113 is preferably a movable plastic wheel, or an omni-wheel and the like.

The pole assembly 120 is preferably a single upright, fixed-height, and non-retractable hollow circular tube, or a group of telescopic rods composed of multiple sections of hollow sleeves and a solid vertical rod, or a multi-link structural member composed of multiple hollow or solid links. The pole assembly 120 having a fixed height preferably has a length ranging from 70 cm to 100 cm, and pole assembly 120 having an adjustable ground height has a length ranging from 50 cm to 120 cm. The shape of the pole assembly 120 is preferably, but not limited to, round, square or other suitable shapes. The pole assembly 120 can be made of, but not limited to, stainless steel, aluminum alloy, plastic material, or composite material. If the pole assembly 120 is a hollow tube, the space contained in it can provide various types of wires, tubes, or component modules to be disposed, arranged or distributed therein, such as, but not limited to, electrical wires, network cables, data bus lines, and battery modules, etc. In the first embodiment disclosed in FIG. 1, the pole assembly 120 is connected to the plugging sleeve 112 on the mobile base 110, and is tightly assembled with mobile base 110 to stand upright from the mobile base 110. In the second embodiment disclosed in FIG. 2, the pole assembly 120 is directly inserted into the plug-in opening on the mobile base 110, fixed to the mobile base 110 through screws and nuts.

The flexible arm 130 is preferably one set of hollow metal hose having a gooseneck assembly or a coiled assembly, preferably made of, but not limited to, a combination of stainless steel wire and a copper alloy wire, which can flex or bend in response to external forces. The internal space of the hollow hose can provide various types of wires, tubes, or component modules to be disposed, arranged or distributed therein, such as, but not limited to, electrical wires, network cables, data bus lines, and battery modules, etc. The first end 131 of the flexible arm 130 is connected to the pole assembly 120 by means of screws, nuts, or welding, and is fixed to the pole assembly 120. The second end 132 is provided with a mobile device connector 140 for various mobile devices 200 such as, but not limited to, a tablet device or a smartphone to connect to the cart 100. In the first embodiment disclosed in FIG. 1, the mobile device 200 is a tablet device. In the second embodiment disclosed in FIG. 2, the mobile device 200 is a smartphone. When the user mounts the mobile device onto the flexible arm 130, the flexible arm 130 flexing and bending in response to the external force allows the user to manually adjust the mobile device 200 to the most appropriate ground height and position.

The first accessory connector 150 is used to connect a multi-purpose platform 151, the second accessory connector 160 is used to connect one set of push handle 161, and the third accessory connector 170 is used to connect one set of device convenient carrier 171, all to the pole assembly 120 and the cart 100 in a movable way. In addition, the ground clearance heights of the first accessory connector 150, the second accessory connector 160, and the third accessory connector 170 on the pole assembly 120 are all adjustable, and can be freely adjusted by the user according to the use situation. Therefore, through the joint operation of the mobile base 110, the pole assembly 120, and the flexible arm 130, the pole assembly 120 and the flexible arm 130 of the cart 100 can have a maximum height of 160 cm or 170 cm after being fully straightened, and preferably providing users with free adjustment of ground clearance heights in the range from 50 cm to 170 cm or from 60 cm to 160 cm.

In actual use, the user can maintain the mobile device 200 at an appropriate ground height by adjusting the flexible arm 130 according to the on-site use situation, and through adjusting the first accessory connector 150, the second accessory connector 160, and the third accessory connector 170, the multi-purpose platform 151, the push handle 161, and the device convenient carrier 171 can be respectively adjusted to different ground clearance heights for operation. The cart 100 in accordance with the present invention can provide various devices and accessories to the user for operation at different heights from the ground level, and provide the user with multiple adjustable degrees of freedom and the best flexibility, which is very suitable for applications in the fields of medical treatment and nursing, etc. to respond to various special and emergency situations.

The external surfaces of the mobile base 110, the pole assembly 120, the flexible arm 130, the mobile device connector 140, the first accessory connector 150, the second accessory connector 160, the third accessory connector 170, and other components included in the cart 100 can be further surface treated to make the surface have special functions such as hydrophobic, hydrophilic, scratch-resistant, abrasion-resistant, antiskid, dustproof, antibacterial, or sterilization in order to adapt to the environment of medical treatment and nursing fields.

Figure 3:
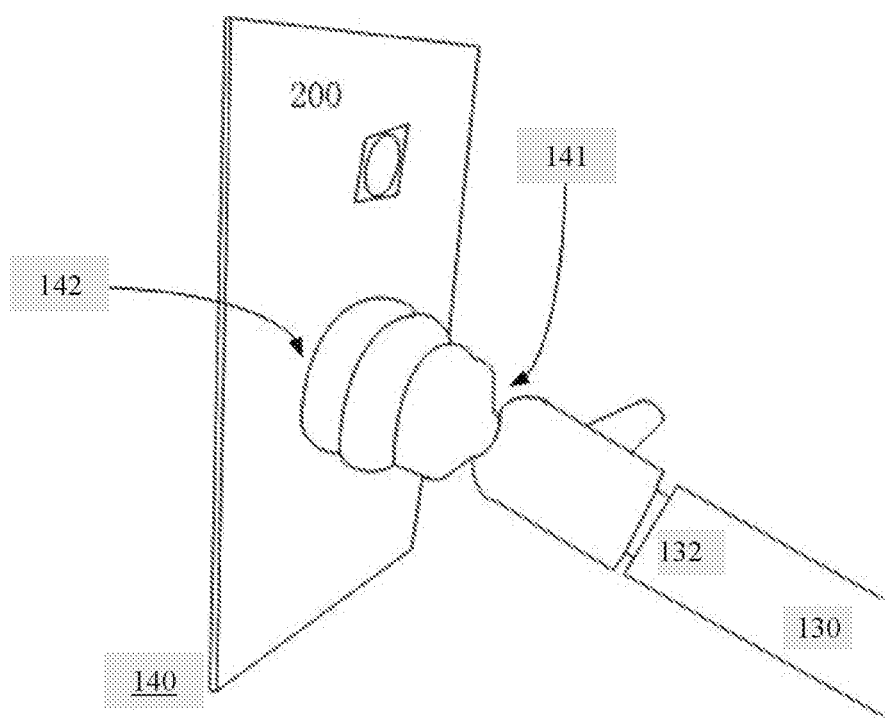
FIG. 3 is a schematic three-dimensional structure diagram illustrating the mobile device connector and the mobile device in a connected state in accordance with the present invention.

FIG. 3 is a schematic three-dimensional structure diagram illustrating the mobile device connector and the mobile device in a connected state in accordance with the present invention. In one embodiment, the mobile device connector 140, taken as an example, is installed on the second end 132 of the flexible arm 130, and includes one set of universal joint 141 and one set of vacuum suction cup 142 or a magnetic suction tenon. The vacuum suction cup 142 is adsorbed on the flat portion on the back of the mobile device 200 to tightly but movably connect to the mobile device 200 and fix to the flexible arm 130 and the cart 100. The flexible arm 130 enables the height of the mobile device 200 from the ground level to be adjusted at any time, and has height-adjustable feature. The universal joint 141 enables the mobile device 200 to turn in any direction and at any angle, and has feature of multiple adjustable degrees of freedom. During the use of the cart 100, the user can freely adjust the mobile device 200 at any time, such that the mobile device 200 can adapt to the user's operation from any direction and any angle, providing the user with extremely high flexibility and convenience.

Figure 4:
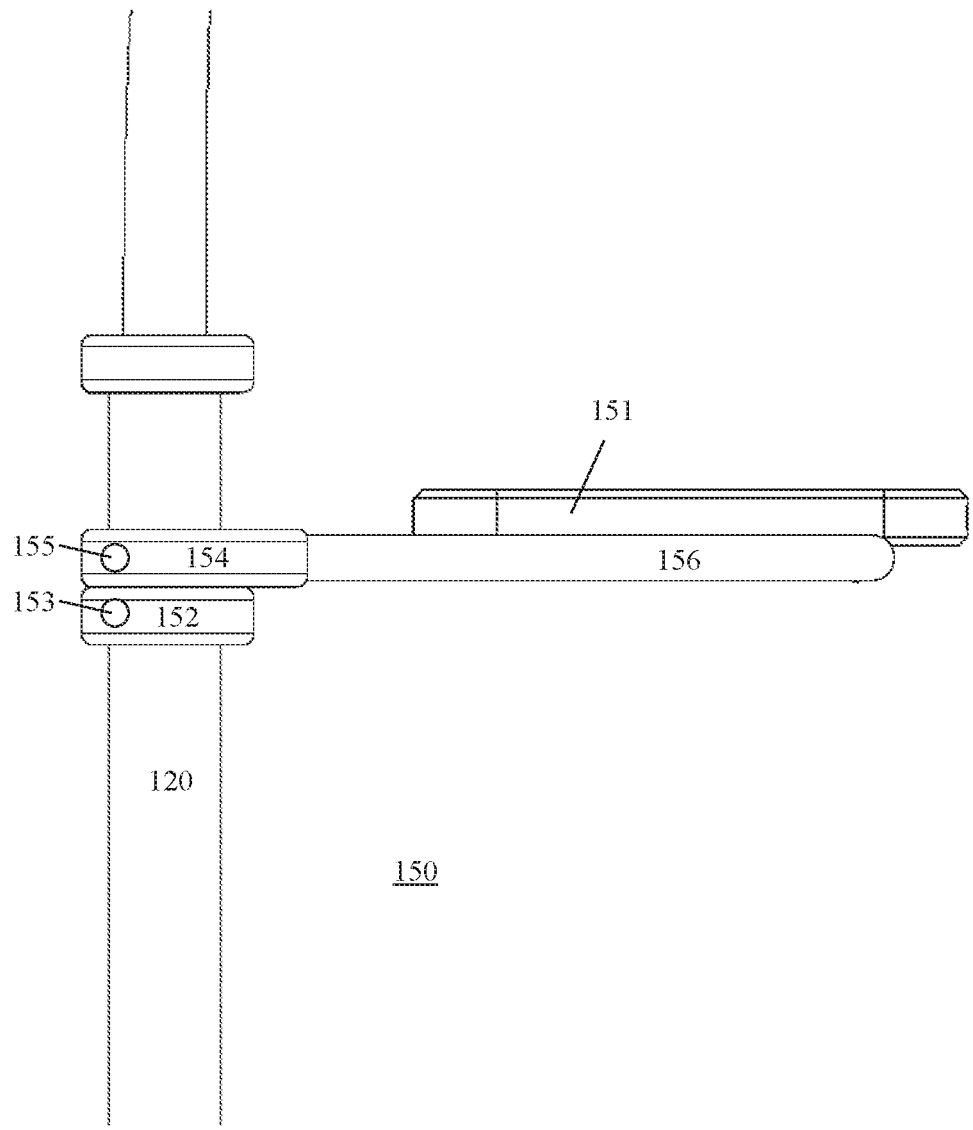
FIG. 4 is a schematic side structure diagram illustrating the first accessory connector and the multi-purpose platform in a connected state in accordance with the present invention.

FIG. 4 is a schematic side structure diagram illustrating the first accessory connector and the multi-purpose platform in a connected state in accordance with the present invention. In one embodiment, the first accessory connector 150, taken as an example, is used to provide support for a horizontal support arm 156. The multi-purpose platform 151 can be assembled on the horizontal support arm 156, such that the multi-purpose platform 151 can be movably connected and fixed to the pole assembly 120 and the cart 100. The first accessory connector 150 includes a height adjustment ring 152, a height adjustment screw 153, a horizontal rotation joint 154, an angle adjustment screw 155, and a horizontal support arm 156. The first accessory connector 150 is an optional component. The first accessory connector 150 can be optionally configured on the cart 100, or not configured on the cart 100.

The horizontal support arm 156 is fixed on the horizontal rotation joint 154. The height adjustment ring 152 provides support for the horizontal support arm 156 and the horizontal rotation joint 154, such that the horizontal support arm 156 and the horizontal rotation joint 154 can be kept at a fixed height from the ground level. When the horizontal support arm 156 and the horizontal rotation joint 154 are adjusted to the ground clearance height required by the user, the height position of the height adjustment ring 152 on the pole assembly 120 can be fixed by locking the height adjustment screw 153 to provide the ground clearance height required by the user. Loosening the height adjustment screw 153 can readjust the height of the height adjustment ring 152 on the pole assembly 120, while the horizontal rotation joint 154 allows the horizontal support arm 156 to rotate 360 degrees. When the horizontal support arm 156 rotates to the angle required by the user, the horizontal support arm 156 can be fixed at the required angle by locking the angle adjustment screw 155, thereby adjusting the angle of use and the ground clearance height of the multi-purpose platform 151. The multi-purpose platform 151 provides a flat working plane capable of placing vital sign sensing devices and sundries, or serving as a writing platform.

Figure 5:
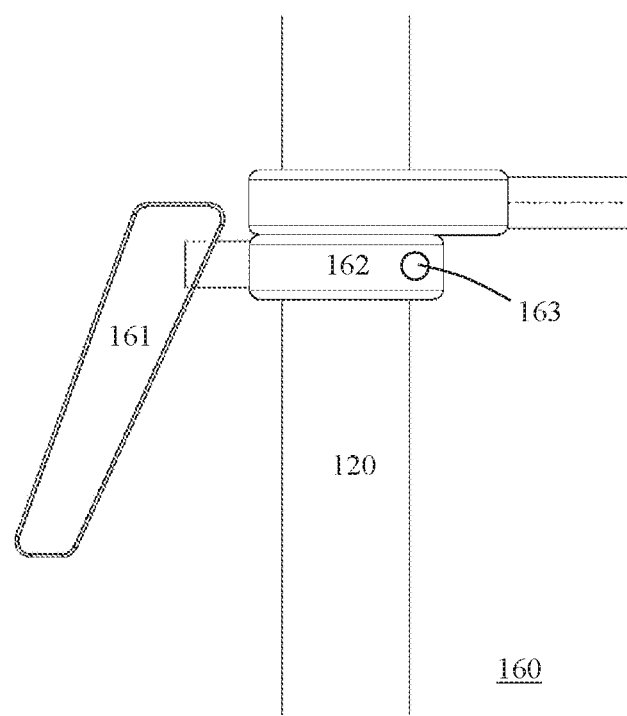
FIG. 5 is a schematic side structure diagram illustrating the second accessory connector and the push handle in a connected state in accordance with the present invention.

FIG. 5 is a schematic side structure diagram illustrating the second accessory connector and the push handle in a connected state in accordance with the present invention. In one embodiment, the second accessory connector 160, taken as an example, is used to provide support to one set of push handle 161 for movably connecting to the pole assembly 120 and the cart 100. The second accessory connector 160 includes a height and angle adjustment ring 162, and a height and angle adjustment screw 163 and the like. The second accessory connector 160 is an optional component. The second accessory connector 160 can be optionally configured on the cart 100, or not configured on the cart 100.

The push handle 161 is directly fixed on the height and angle adjustment ring 162. The height and angle adjustment ring 162 provides support for the push handle 161, and provides the push handle 161 to simultaneously adjust the ground clearance height and the angle of use on the cart 100, such that the push handle 161 can be kept at a fixed ground clearance height and a specific angle of use. When the push handle 161 and the height and angle adjusting ring 162 are adjusted to the ground clearance height and the angle of use required by the user, the height and angle adjustment ring 162 can be fixed on a certain height of the pole assembly 120 by locking the height and angle adjusting screw 163, in order for the push handle 161 to provide the ground clearance height and the angle of use required by the user. Loosening the height and angle adjustment screw 163 can readjust the height and angle adjustment ring 162, and the ground clearance height and the angle of use of the push handle 161 on the pole assembly 120. The push handle 161 is used as a force applying handle, such that the user can exert force to move the cart 100 by hands.

Figure 6:
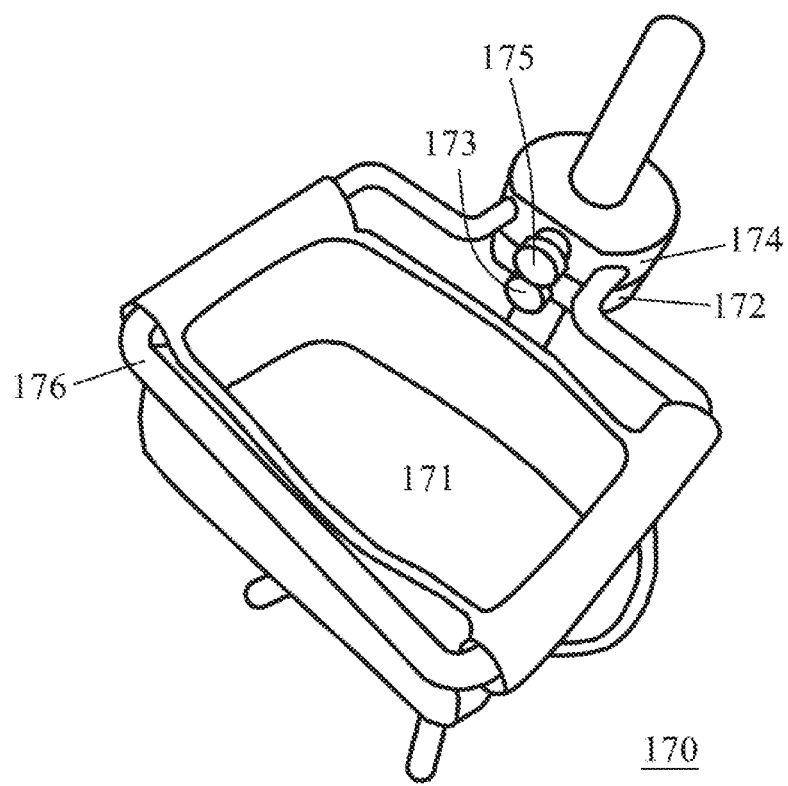
FIG. 6 is a schematic three-dimensional structure diagram illustrating the third accessory connector and the device convenient carrier in a connected state in accordance with the present invention.
Figure 7:
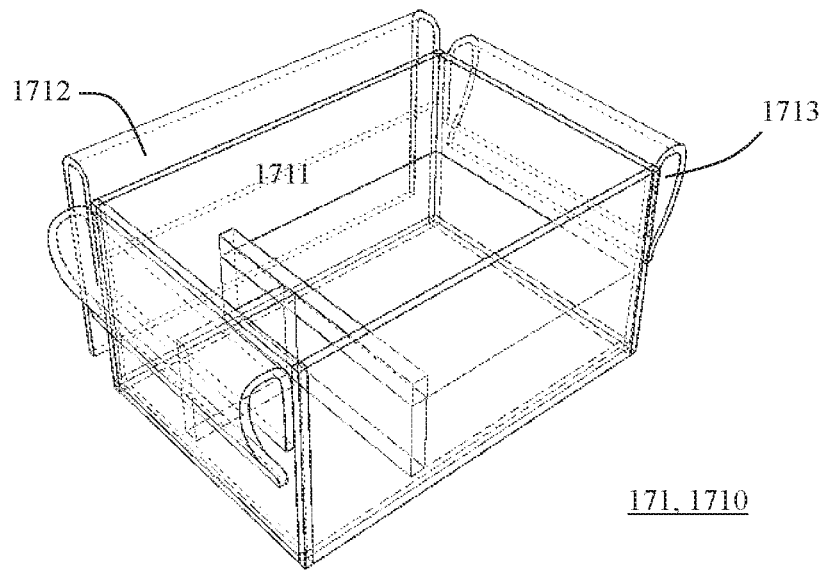
FIG. 7 and FIG. 8 are schematic three-dimensional structure diagrams illustrating the device convenient carrier in accordance with the present invention.
Figure 8:
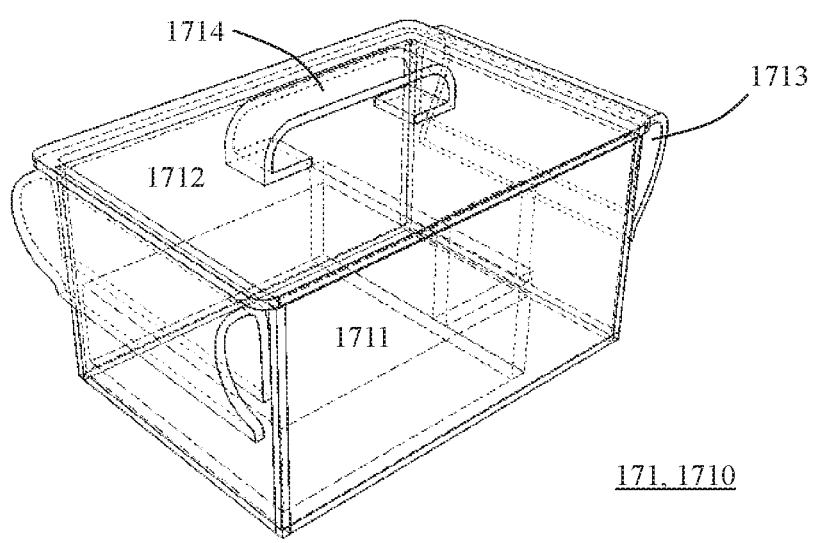

FIG. 6 is a schematic three-dimensional structure diagram illustrating the third accessory connector and the device convenient carrier in a connected state in accordance with the present invention. FIG. 7 and FIG. 8 are schematic three-dimensional structure diagrams illustrating the device convenient carrier in accordance with the present invention. In one embodiment, the third accessory connector 170, taken as an example, is used to provide support for one set of annular bracket 176 or a horizontal bracket. One set of device convenient carrier 171 is connected to the annular bracket 176, such that one set of device convenient carrier 171 can be movably connected to the pole assembly 120 and the cart 100. The third accessory connector 170 includes a height adjustment ring 172, a height adjustment screw 173, a horizontal rotation joint 174, an angle adjustment screw 175, and an annular bracket 176, etc. The third accessory connector 170 is an optional component. The third accessory connector 170 can be optionally configured on the cart 100, or not configured on the cart 100.

Similarly, the annular bracket 176 is fixed on the horizontal rotation joint 174. The height adjustment ring 172 provides support for the annular bracket 176 and the horizontal rotation joint 174, such that the annular bracket 176 and the horizontal rotation joint 174 can be kept at a fixed ground clearance height. When the annular bracket 176 and the horizontal rotation joint 174 are adjusted to the ground clearance height required by the user, the height position of the height adjustment ring 172 on the pole assembly 120 can be fixed by locking the height adjustment screw 173 to provide the ground clearance height required by the user. Loosening the height adjustment screw 173 can readjust the height position of the height adjustment ring 172 on the pole assembly 120, while the horizontal rotation joint 174 allows the annular bracket 176 to rotate 360 degrees. When the annular bracket 176 is turned to the angle required by the user, the annular bracket 176 can be fixed at the required angle by locking the angle adjustment screw 175, thereby adjusting the angle of use and the ground clearance height of the device convenient carrier 171.

The device convenient carrier 171 connected to the annular bracket 176 is an apparatus for placing and storing vital sign sensing devices such as, but not limited to, a multi-parameter physiological signal monitor, a pulse oximeter, a portable electrocardiograph, a vital sign machine, a sphygmomanometer, an oximeter, a blood glucose meter, a heartbeat meter, a thermometer, a forehead thermometer, a body fat monitor, and a multi-functional smart measurement phone, etc. Preferably, it can be a carrying basket, a carrying bag, a basket, a bag, and the material includes cloth, non-woven fabric, latex cloth, plastic, or a mixture of the above components.

In one embodiment, the device convenient carrier 171 shown in FIG. 6 is preferably taken a bag as an example but not limited to a bag, which includes a plurality of partitioned spaces for placing and storing the vital sign sensing devices, and is mounted on the annular bracket 176 through the Velcro straps on both sides. In another embodiment, the device convenient carrier 171 shown in FIG. 7 and FIG. 8 is preferably taken a carrying bag 1710 as an example but not limited to a carrying bag, which includes a bag body 1711 and an upper cover 1712. A handle 1714 is provided on the upper cover 1712, and Velcro straps 1713 are arranged on both sides of the bag body 1711. To serve as the carrying bag 1710 of the device convenient carrier 171, the carrying bag 1710 can be simply mounted on the annular bracket 176 through the Velcro straps 1713, thus movably connecting to the pole assembly 120 and the cart 100. When the carrying bag 1710 is removed from the annular bracket 176, the user only needs to close the upper cover 1712 and the bag body 1711, and then the carrying bag 1710 can be taken away through grasping the handle 1714 for other purposes.

Figure 9:
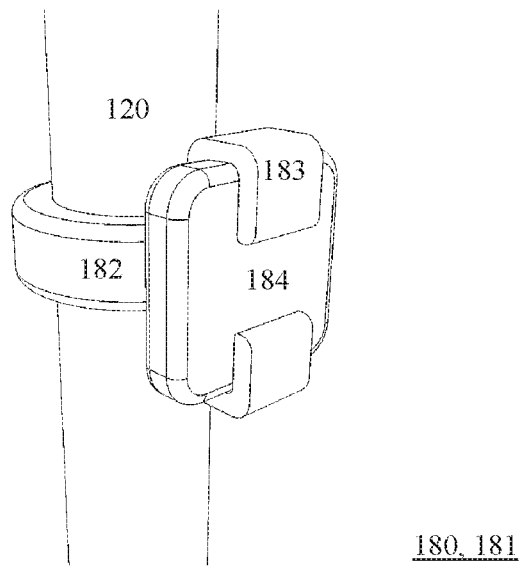
FIG. 9 is a schematic three-dimensional diagram illustrating the fourth accessory connector in accordance with the present invention.
Figure 10:
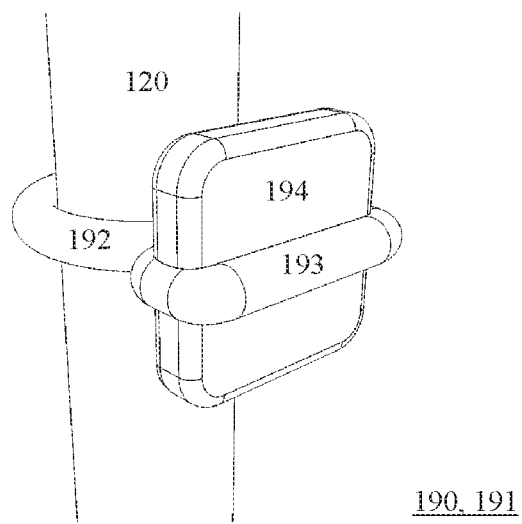
FIG. 10 is a schematic three-dimensional diagram illustrating the fifth accessory connector in accordance with the present invention.

FIG. 9 is a schematic three-dimensional diagram illustrating the fourth accessory connector in accordance with the present invention. In one embodiment, the fourth accessory connector 180, taken as an example, is preferably a buckle member 181, including a first buckle base 182 for gripping the pole assembly 120 and an idle second buckle seat 183. The first buckle seat 182 and the second buckle seat 183 are disposed on opposite sides of the buckle member 181. An electronic timer 184 is embedded in the buckle seat 183 in this embodiment. FIG. 10 is a schematic three-dimensional diagram illustrating the fifth accessory connector in accordance with the present invention. In one embodiment, the fifth fitting connector 190, taken as an example, is preferably a simple fixing ring 191, including a retaining strip 192 for gripping the pole assembly 120 and an idle elastic strip 193. The retaining strip 192 and the elastic strip 193 are disposed on opposite sides of the simple fixing ring 191. An electronic pedometer 194 is embedded in the elastic strip 193 in this embodiment.

The pole assembly 120 preferably also includes a series of laterally or longitudinally distributed groove structures, convex structures, or concave structures to serve as the positioning points and the mounting points, which can assist the positioning of the first accessory connector 150, the second accessory connector 160, the third accessory connector 170, the fourth accessory connector 180, and the fifth accessory connector 190, etc. on the pole assembly 120, or provide additional mounting points for more accessories to be connected to the cart 100.

A plurality of connectors distributed on the cart 100 including a mobile device connector 140, a first accessory connector 150, a second accessory connector 160, a third accessory connector 170, a fourth accessory connector 180, and a fifth accessory connector 190, etc. are a group of components having connection or support functions, such that various accessories, apparatuses, and additional devices such as, but not limited to, multi-purpose platform, push handle, support frame, and mobile device, etc. can be attached, connected and fixed to cart 100 in a temporary, movable, detachable or separable manner. Some of these connectors include various connecting elements, whereas the other connectors include various supporting elements. Various connecting elements are, but not limited to, buckle element, fastening element, clasping element, clamper, fastener, clamping element, engaging element, screw, screw fastener, locking element, tenon, buckle strap, retaining ring, elastic ring, rope connector, Velcro strap, suction cup, or magnet, etc. Various supporting elements are, but not limited to, horizontal support element, lateral support rod, support rod, ring bracket, horizontal bracket, hook, lifting ring, tenon, and retaining ring, etc.

Figure 11:
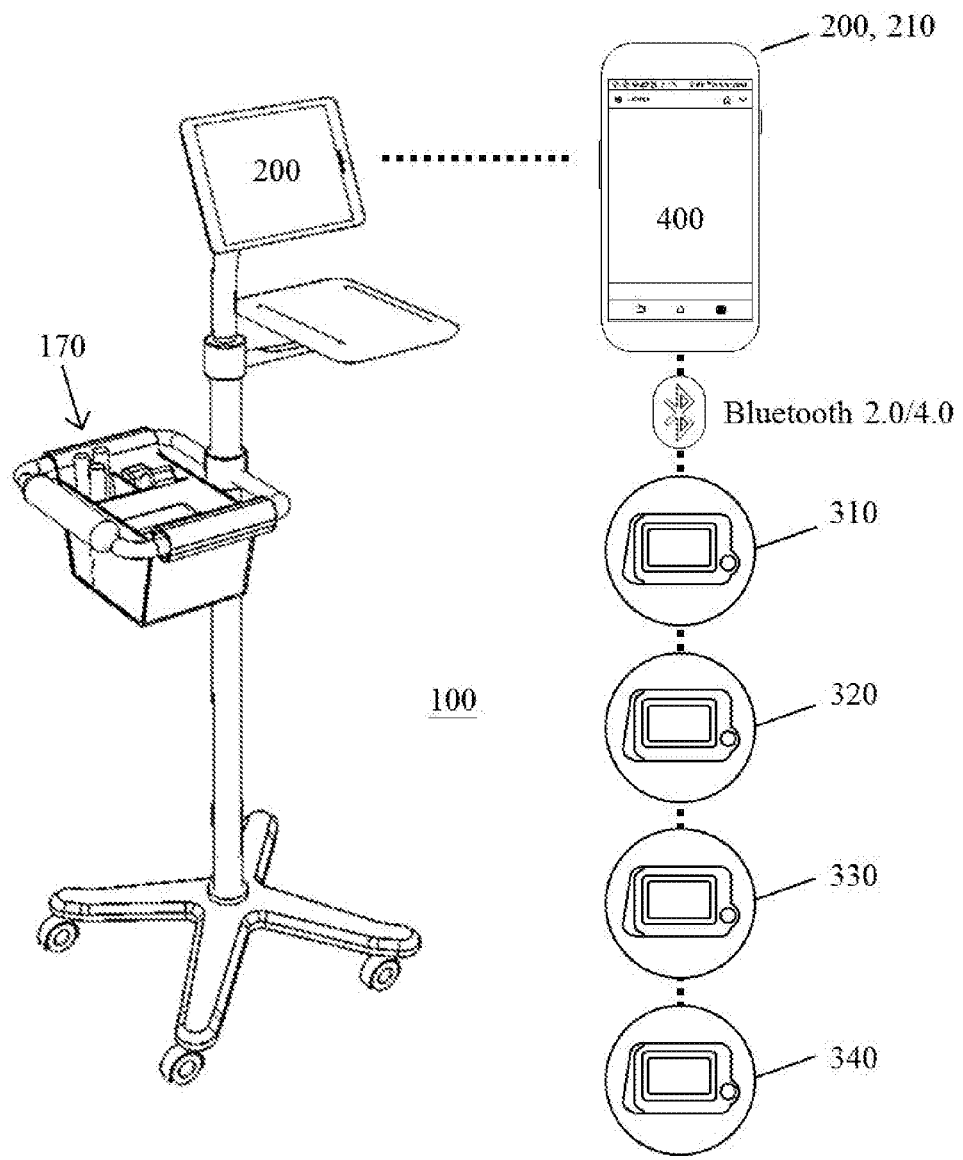
FIG. 11 is a conceptual diagram illustrating a local IoT eco-system consisting of the smart mobile cart for nursing and caring in accordance with the present invention and multiple kinds of vital sign sensing devices carried thereby.

FIG. 11 is a conceptual diagram illustrating a local IoT eco-system consisting of the smart mobile cart for nursing and caring in accordance with the present invention and multiple kinds of vital sign sensing devices carried thereby. The mobile device 200, attached to the smart mobile cart 100 in accordance with the present invention, is preferably installed with a smart nursing information platform, which is an information technology platform designed and developed by the same present applicant and fully disclosed in the Taiwan Invention Patent Application Serial No. 107134372 with an invention name of "Smart Text of Nursing Generating System Based on Lexical Analysis and Smart Nursing Information Platform Using the Same" filed on Sep. 28, 2018, and in the Taiwan Invention Patent Application Serial No. 107134427 with an invention name of "Mobile Care Information System Based on Instant Messaging" filed on Sep. 28, 2018, which are incorporated into this application by reference as if fully set forth herein.

In this embodiment, the mobile device 200 is, but not limited to, a smart phone 210 mounted with a smart care platform 400. Between the smart phone 210 and various vital sign sensing devices in this embodiment are, but not limited to, a multifunctional vital sign machine 310, a multi-parameter vital sign machine 320, a blood pressure meter 330, and a blood glucose meter 340 through various wireless communication technologies or protocols such as, but not limited to, Bluetooth 2.0, Bluetooth 4.0, Bluetooth 4.1. Bluetooth 4.2. Bluetooth 5.0. Bluetooth Low Energy (BLE), Zigbee, Wi-Fi, HiperLAN, Sub-1 GHz RF technology, 2.4 GHz RF technology, or home RF technology. In this embodiment, Bluetooth 2.0/4.0 technology is selected to establish a wireless communication connection between the smartphone 210 and various vital sign sensing devices.

In this embodiment, devices such as a multifunctional vital sign machine 310, a multi-parameter vital sign machine 320, a blood pressure meter 330, and a blood glucose meter 340 are designed to be small, portable, and networked. Through Bluetooth 2.0/4.0 and the smart phone 210, a wireless ad hoc network can be established immediately at any time and at any place. When a wireless communication link is established between the smart phone 210 and various vital sign sensing devices, the vital sign parameters measured by each vital sign sensing device can be directly transmitted to the smart care platform 400 on the smart phone 210 in real time. While the user operates the vital sign sensing device to complete the vital sign measurement of the care recipient, the measured data have been synchronously recorded on the system, so the user does not need to unnecessarily copy and record the measured data many times.

Therefore, the smart mobile cart 100 in accordance with the present invention can be regarded as a small hub of the IoT, which can centralize the nodes established by various vital sign sensing devices to the mobile device of the mobile cart, which is very suitable for use in a local area such as, but not limited to, mobile nursing station, smart nursing station, general nursing station, bedside care, home care, elderly care, clinical use, personal care, long-term care, care center and other areas of use. With the smart care platform 400 having an open interface, medical and household instruments can be integrated, and with Bluetooth as an interface, information automatic transmission service is enhanced to integrate the networked vital sign sensing devices used in medical treatment, nursing and care to the smart mobile cart 100 in accordance with the present invention to provide user for operation.

By immediately uploading the measured vital sign data to the system such as, but not limited to, a mobile care information system combined with the instant messaging (IM) included in the smart care platform 400, the real-time vital signs of the care recipient can be provided to the institutional end, the family end, or anyone authorized to receive the vital signs. In conjunction with the filtering and screening of the artificial intelligence module in the smart care platform 400, abnormal and urgent vital signs, if detected, can be sent to the institutional end in different levels of urgency at the first time, thus avoiding delayed notification of emergency and reducing human negligence. For the family members, they can receive the latest life signs of their family members regularly as well as immediately, thereby establishing a positive communication relationship with the institutional end without a sense of alienation any more. In contrast, the existing tools cannot assist the care institutions to deliver and integrate health care information in real time. In such a state of incomplete information, it is also difficult for the institutions to establish a positive communication relationship between the elderly, the family members and the institutional staff.

Figure 12:
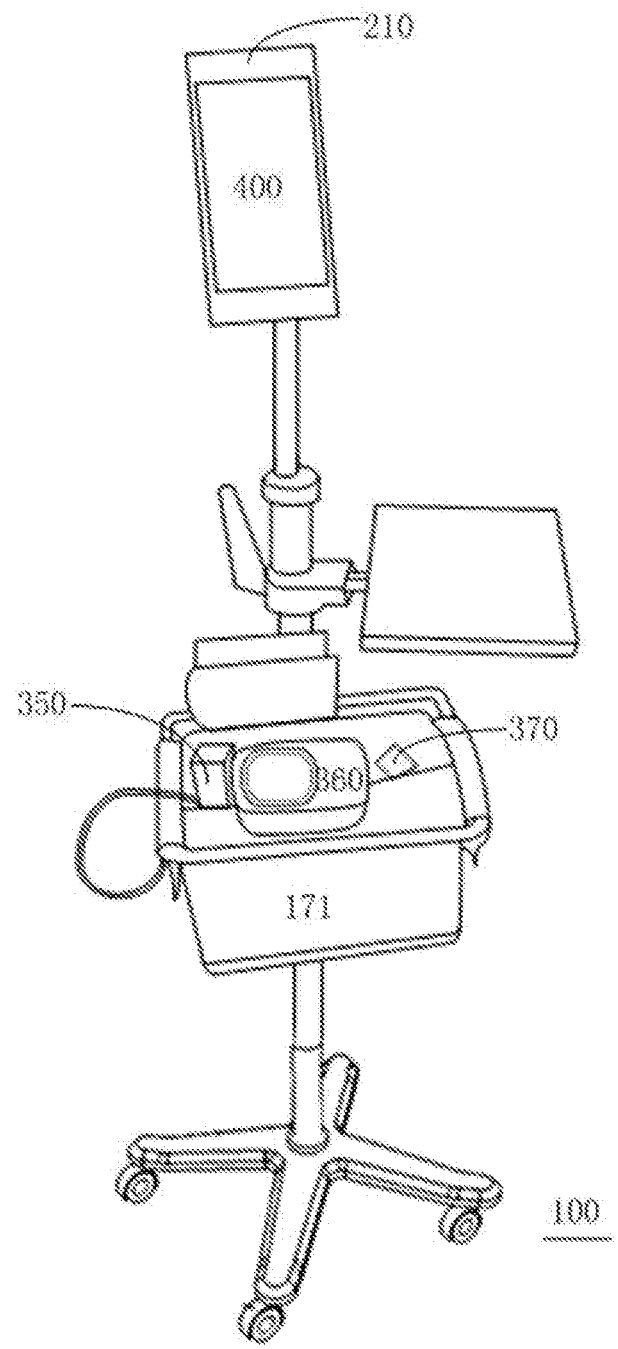
FIG. 12 is a schematic diagram illustrating the nursing smart cart in accordance with the present invention in a standby state.
Figure 13:
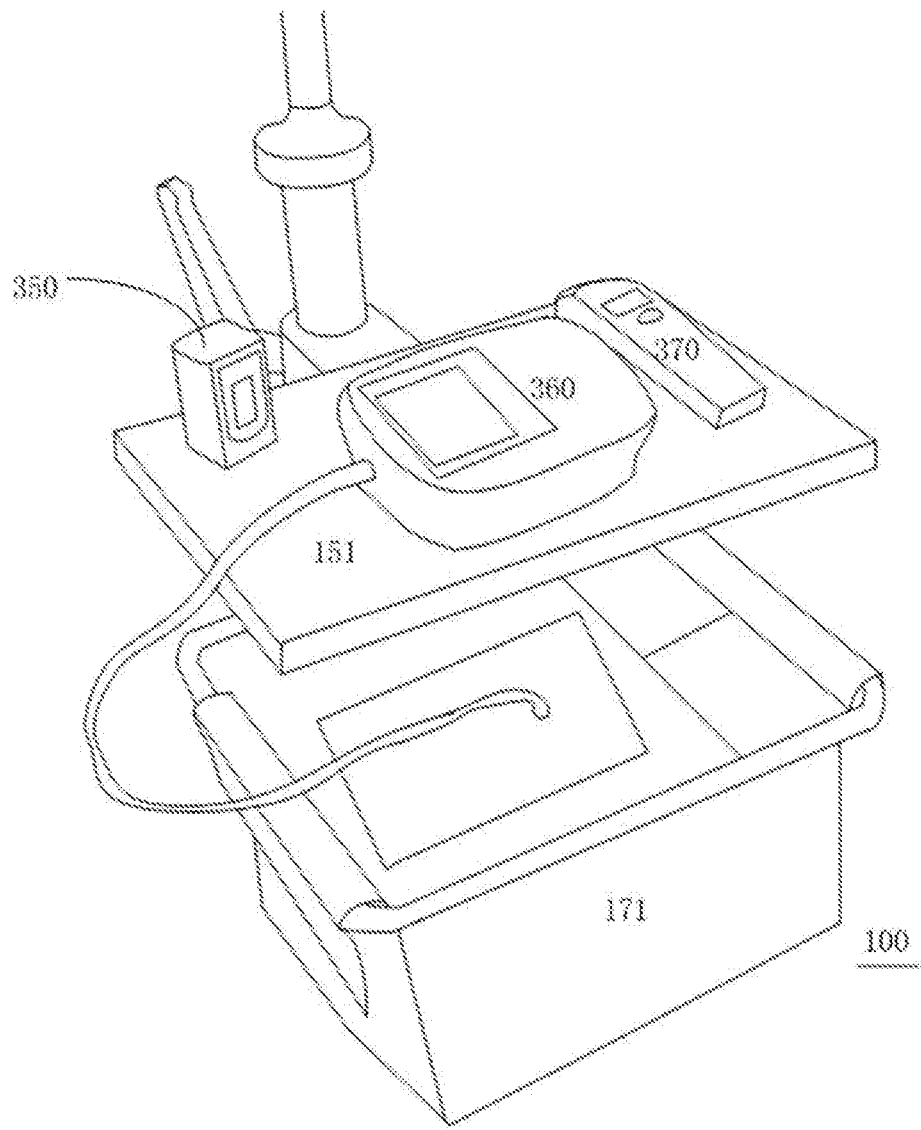
FIG. 13 is a schematic diagram illustrating the first use state of the nursing smart cart in accordance with the present invention.
Figure 14:
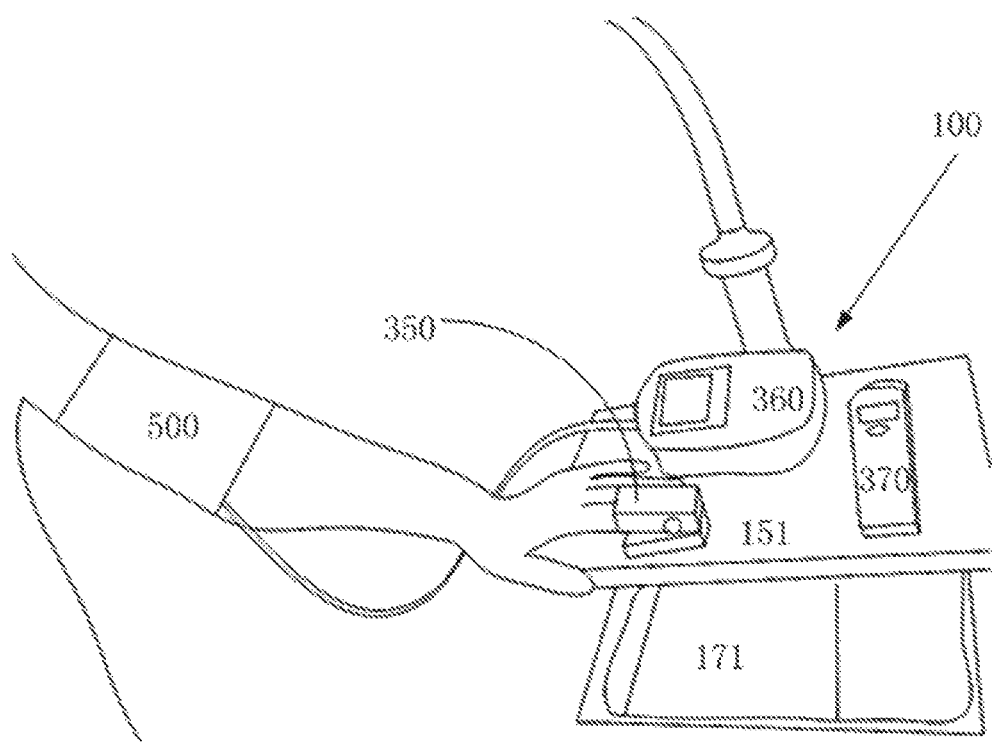
FIG. 14 is a schematic diagram illustrating the second use state of the nursing smart cart in accordance with the present invention.

FIG. 12 is a schematic diagram illustrating the nursing smart cart in accordance with the present invention in a standby state; FIG. 13 is a schematic diagram illustrating the first use state of the nursing smart cart in accordance with the present invention; FIG. 14 is a schematic diagram illustrating the second use state of the nursing smart cart in accordance with the present invention. As shown in FIG. 12, when the nursing smart cart 100 in accordance with the present invention is in use, the smart phone 210 has been mounted on the cart 100. The user has turned on the smart care platform 400 mounted on the smart phone 210, and the vital sign sensing devices such as, but not limited to, finger clip type pulse oximeter 350, arm type sphygmomanometer 360, infrared ear thermometer 370, have also been put in the device convenient carrier 171 of the nursing smart mobile cart 100 in accordance with the present invention. However, in this embodiment, the finger clip type pulse oximeter 350, the arm type sphygmomanometer 360, and the infrared ear thermometer 370 are not network-connectable devices.

As shown in FIG. 13, when in use, the user adjusts the multi-purpose platform 151 and the device convenient carrier 171 to the appropriate use angle and the ground clearance height, respectively, and then removes the finger clip type pulse oximeter 350, the arm type sphygmomanometer 360, and the infrared ear thermometer 370 from the device convenient carrier 171 to the multi-purpose platform 151. As shown in FIG. 14, the user starts to use the finger clip type pulse oximeter 350 and the arm type sphygmomanometer 360 to measure the vital sign parameters such as blood oxygen concentration and blood pressure for the care recipient 50X), and immediately and directly inputs the relevant vital sign data to the nearby smart care platform 400 on the smart phone 210 mounted on the cart 100, thus saving many unnecessary and repeated handwritten transcriptions by the user.

In practical use, the nursing smart cart 100 in accordance with the present invention can provide the mobile device 200 to adjust the ground clearance height in the range of about 120 cm to 170 cm for the user to operate, and provide various vital sign sensing devices such as, but not limited to, finger clip type pulse oximeter 350, arm type sphygmomanometer 360, and infrared ear thermometer 370 to adjust the ground clearance height in the range of about 50 cm to 120 cm for the user or the care recipient to operate. As a whole, the mobile cart 100 can allow the mobile device 200 and various vital sign sensing devices to adjust the ground clearance height in the range of 50 cm to 170 cm or in the range of 60 cm to 160 cm, and provide users or care recipients with different ground clearance heights for them to operate.

Figure 15:
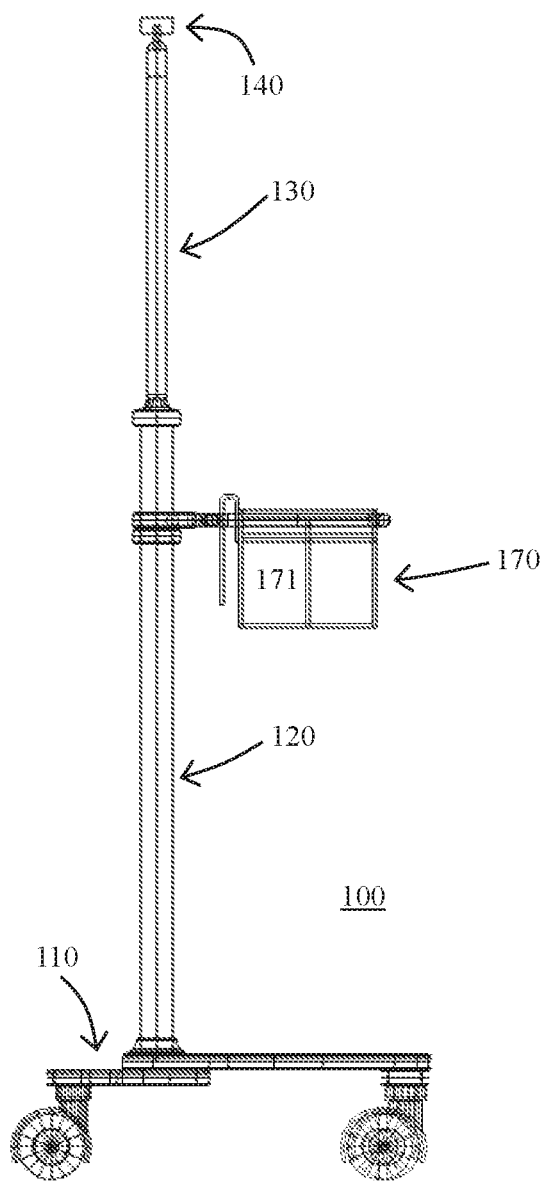
FIG. 15 is a schematic side structure diagram illustrating a third embodiment for the nursing and caring smart mobile cart in accordance with the present invention.

FIG. 15 is a schematic side structure diagram illustrating a third embodiment for the nursing and caring smart mobile cart in accordance with the present invention. In this embodiment, the smart mobile cart 100 disclosed in accordance with the present invention includes: a mobile base 110, a first pole 121, a second pole 133, a mobile device connector 140, an optional third accessory connector 170, and a device convenient carrier 171, wherein the first pole 121 has two ends, one of which the two ends is connected with the mobile base 110 and stands upright from the mobile base 110 and the other one of which the two ends is connected with one of two ends of the second pole 133. The other one of the two ends of the second pole 133 has configured with the mobile device connector 140. Any mobile device is able to be attached to the smart mobile cart 100 through the mobile device connector 140.

The third accessory connector 170 is connected to the first pole 121 in a movable way. Third accessory connector 170 provides for the device convenient carrier 171 to connect to the smart mobile cart 100 through the third accessory connector 170. The device convenient carrier 171 is an apparatus for placing and storing various vital sign sensing devices and rendering these vital sign sensing devices capable of being placed and attached to the smart mobile cart 100. Through the joint operation of the first pole 121, the second pole 133, and the third accessory connector 170, the mobile device straightforwardly connected to the smart mobile cart 100 through the mobile device connector 140, and the vital sign sensing devices placed in device convenient carrier 171 can have a height above ground level adjustable in a range from 50 cm to 170 cm or from 60 cm to 160 cm above from the ground level, for providing for users to use or operate at different ground clearance heights respectively.

In particular, the joint configuration of the first pole 121, the second pole 133, and the third accessory connector 170, enables the mobile device connector 140 and the device convenient carrier 171 being capable of adjusting a height above ground level in a range from 50 cm to 170 cm, or in a range from 60 cm to 160 cm, so as to provide for users to use or operate at different ground clearance heights respectively. For instance, providing a mobile device for nursing staff to operate at a height above ground level of about 120 cm, or providing a vital sign sensing device for a caring subject or a patient to measure heart rate or blood pressure, etc., at a height above ground level of about 70 cm.

There are further embodiments provided as follows.

Embodiment 1

A smart mobile cart for nursing and caring includes: a pole assembly standing upright from a mobile base and having two ends, one of which the two ends is connected with the mobile base; a flexible arm having two ends, one of which the two ends is connected with the pole assembly and another end is configured with a device connector, to render a mobile device attached to the smart mobile cart through the device connector; and an accessory connector connected with the pole assembly in a movable and detachable means and providing for a device convenient carrier to connect with the smart mobile cart through the accessory connector, whereby a vital sign sensing device is placed on the smart mobile cart through the device convenient carrier, wherein the pole assembly, the flexible arm, and the accessory connector are configured to have a height above from a ground level adjustable, so as to provide the mobile device and the vital sign sensing device at different ground clearances respectively for a user to operate.

Embodiment 2

The smart mobile cart as claimed in Embodiment 1, further includes: a first accessory connector, connected to the pole assembly in a movable and detachable means and providing for a desk to secure to the smart mobile cart; a second accessory connector, connected to the pole assembly in a movable and detachable means and providing for a handle to secure to the smart mobile cart; a fourth accessory connector, connected to the pole assembly in a movable and detachable means and providing for a mounting base to attach to the smart mobile cart, wherein the buckle base provides for a fourth accessory to affix to the smart mobile cart in a releasable retaining means; and a fifth accessory connector, connected to the pole assembly in a movable and detachable means and providing for an elastic band to attach to the smart mobile cart, wherein the elastic band provides for a fifth accessory to affix to the smart mobile cart in a fastening means.

Embodiment 3

The smart mobile cart as claimed in Embodiment 2, the device connector, the accessory connector, the first accessory connector, the second accessory connector, the fourth accessory connector and the fifth accessory connector are a universal joint, a vacuum suction cup, a magnetic suction tenon, a horizontal rotation joint, a height adjustment ring, a simple fixing ring, a retaining strip, an elastic strip, a buckle member, a fastening element, a clasping element, a clamper, fastener, a clamping element, an engaging element, a screw, screw fastener, a locking element, a tenon, a buckle strap, a retaining ring, an elastic ring, a rope connector, a Velcro strap, a suction cup, a horizontal support element, a lateral support rod, a support rod, a ring bracket, a horizontal bracket, a hook, or a lifting ring.

Embodiment 4

The smart mobile cart as claimed in Embodiment 2, the device convenient carrier is a carrying basket, a carrying bag, a basket, or a bag.

Embodiment 5

The smart mobile cart as claimed in Embodiment 2, the mobile device is a tablet device, a smart phone or a touch interface device.

Embodiment 6

The smart mobile cart as claimed in Embodiment 2, the pole assembly includes a groove, a slot, a protrusion or a recess formed thereon.

Embodiment 7

The smart mobile cart as claimed in Embodiment 2, the vital sign sensing device is a multi-parameter physiological signal monitor, a pulse oximeter, a portable electrocardiograph, a vital sign machine, a sphygmomanometer, an oximeter, a blood glucose meter, a heartbeat meter, a thermometer, a forehead thermometer, a body fat monitor, or a multi-functional smart measurement phone.

Embodiment 8

The smart mobile cart as claimed in Embodiment 2, the mobile base, the pole assembly, the flexible arm, the device connector and the accessory connector have an outer surface with a hydrophobic function, a hydrophilic function, a scratch-resistant function, an abrasion-resistant function, an antiskid function, a dustproof function, an antibacterial function, or a sterilization function.

Embodiment 9

A smart mobile cart for nursing and caring includes: a pole assembly having two ends, one of which the ends connect with a mobile base and stands upright from the mobile base; a flexible arm having two ends, one of which the ends connect with the pole assembly and another is configured with a device connector, to render a mobile device installed with a smart caring platform affixed to the smart mobile cart through the device connector; and an accessory connector, connected with the pole assembly in a movable and detachable means and providing for a device convenient carrier to connect with the smart mobile cart through the accessory connector, to render a vital sign sensing device placed on the smart mobile cart through the device convenient carrier, wherein a wireless communication link is established by configuring a wireless communication protocol between the vital sign sensing device and the mobile device, to render a vital sign signal currently detected by the vital sign sensing device transmitted to the smart caring platform installed on the mobile device in real time.

Embodiment 10

A smart mobile cart for nursing and caring includes: a pole assembly having two ends, one of which the ends connect with a mobile base and stands upright from the mobile base; a support arm having two ends, one of which the ends connect with the pole assembly and another is configured with a device connector, to render a mobile device affixed to the smart mobile cart through the device connector; and an accessory connector, connected with the pole assembly in a movable and detachable means and providing for a device convenient carrier to connect with the smart mobile cart through the accessory connector, to render a vital sign sensing device being placed on the smart mobile cart through the device convenient carrier, wherein by a joint configuration of the pole assembly, the support arm, and the accessory connector, the device connector and the device convenient carrier is enabled to have a height above ground level adjustable so as to provide for a user to operate at different ground clearances respectively.

While the disclosure has been described in terms of what are presently considered to be the most practical and preferred embodiments, it is to be understood that the disclosure need not be limited to the disclosed embodiments. On the contrary, it is intended to cover various modifications and similar arrangements included within the spirit and scope of the appended claims, which are to be accorded with the broadest interpretation so as to encompass all such modifications and similar structures. Therefore, the above description and illustration should not be taken as limiting the scope of the present disclosure which is defined by the appended claims.

What is claimed is:

1. A smart mobile cart for nursing and caring, comprising:
a pole assembly standing upright from a mobile base and having two ends, one end of which the two ends is connected with the mobile base;
a flexible gooseneck tube arm having two ends, one end of which the two ends is connected with the pole assembly and another end is configured with a device connector, to render a mobile device, on which a smart nursing information platform is installed, being attached to the smart mobile cart through the device connector, to enable the mobile device to adaptively and adjustably retain in any position within a scope of a semi-sphere centered upon the one end connected with the pole assembly according to an adjustment operation on demand from a nursing and caregiving user;
an accessory connector connected with the pole assembly by a first quick-release means and providing for an accessory to connect with the smart mobile cart through the accessory connector; and
a vital sign sensing device connector attached to the pole assembly by a second quick-release means and providing for a device convenient carrier to attach onto the smart mobile cart through the vital sign sensing device connector, whereby a vital sign sensing device is placed on the smart mobile cart through the device convenient carrier, wherein the vital sign sensing device is communicatively connected with the mobile device wirelessly to upload a sensed vital sign parameter to the smart nursing information platform in real time,
wherein the vital sign sensing device connector and the accessory connector are configured to have a position and a ground height above from a ground level that are adjustable in either a lengthwise direction or a transverse direction along the pole assembly and work with the flexible gooseneck tube arm, so as to provide the mobile device and the vital sign sensing device at the different position and ground height for a nursing and caregiving user to operate on demands,
wherein the smart nursing information platform further forwards the sensed vital sign parameter to authorized family users via an instant messaging in real time,
wherein when the smart nursing information platform determines the sensed vital sign parameter is an abnormal vital sign by an artificial intelligence module included in the smart nursing information platform, it sends an emergency notification to the nursing and caregiving user and the authorized family users via the instant messaging in real time.

2. The smart mobile cart as claimed in claim 1, further comprising:
a first accessory connector, connected to the pole assembly in a movable and detachable means and providing for a desk to secure to the smart mobile cart;
a second accessory connector, connected to the pole assembly in a movable and detachable means and providing for a handle to secure to the smart mobile cart;
a fourth accessory connector, connected to the pole assembly in a movable and detachable means and providing for a mounting base to attach to the smart mobile cart, wherein the buckle base provides for a fourth accessory to affix to the smart mobile cart in a releasable retaining means; and
a fifth accessory connector, connected to the pole assembly in a movable and detachable means and providing for an elastic band to attach to the smart mobile cart, wherein the elastic band provides for a fifth accessory to affix to the smart mobile cart in a fastening means.

3. The smart mobile cart as claimed in claim 2, wherein the device connector, the accessory connector, the first accessory connector, the second accessory connector, the fourth accessory connector and the fifth accessory connector are selected from a universal joint, a vacuum suction cup, a magnetic suction tenon, a horizontal rotation joint, a height adjustment ring, a simple fixing ring, a retaining strip, an elastic strip, a buckle member, a fastening element, a clasping element, a clamper, fastener, a clamping element, an engaging element, a screw, screw fastener, a locking element, a tenon, a buckle strap, a retaining ring, an elastic ring, a rope connector, a Velcro strap, a suction cup, a horizontal support element, a lateral support rod, a support rod, a ring bracket, a horizontal bracket, a hook, a lifting ring, and a combination thereof.

4. The smart mobile cart as claimed in claim 2, wherein the device convenient carrier is a carrying basket, a carrying bag, a basket, or a bag.

5. The smart mobile cart as claimed in claim 2, wherein the mobile device is a tablet device, a smart phone or a touch interface device.

6. The smart mobile cart as claimed in claim 2, wherein the pole assembly comprises a groove, a slot, a protrusion or a recess formed thereon.

7. The smart mobile cart as claimed in claim 2, wherein the vital sign sensing device is a multi-parameter physiological signal monitor, a pulse oximeter, a portable electrocardiograph, a vital sign machine, a sphygmomanometer, an oximeter, a blood glucose meter, a heartbeat meter, a thermometer, a forehead thermometer, a body fat monitor, or a multi-functional smart measurement phone.

8. The smart mobile cart as claimed in claim 2, wherein the mobile base, the pole assembly, the flexible gooseneck tube arm, the device connector and the accessory connector have an outer surface with a hydrophobic function, a hydrophilic function, a scratch-resistant function, an abrasion-resistant function, an antiskid function, a dustproof function, an antibacterial function, or a sterilization function.

* * * * *